United States Patent
Matharu et al.

(10) Patent No.: US 9,320,781 B2
(45) Date of Patent: Apr. 26, 2016

(54) DIETARY SUPPLEMENT FOR MANAGING GUT HEALTH

(75) Inventors: Kawal Matharu, Auckland (NZ); Iona Weir, Auckland (NZ)

(73) Assignee: VITAL FOODS LIMITED, Auckland (NZ)

( * ) Notice: Subject to any disclaimer, the term of this patent is extended or adjusted under 35 U.S.C. 154(b) by 0 days.

(21) Appl. No.: 14/117,713

(22) PCT Filed: May 16, 2012

(86) PCT No.: PCT/NZ2012/000066
§ 371 (c)(1),
(2), (4) Date: Feb. 18, 2014

(87) PCT Pub. No.: WO2012/158048
PCT Pub. Date: Nov. 22, 2012

(65) Prior Publication Data
US 2015/0037315 A1  Feb. 5, 2015

Related U.S. Application Data

(60) Provisional application No. 61/486,662, filed on May 16, 2011.

(51) Int. Cl.
| | |
|---|---|
| A61K 38/46 | (2006.01) |
| A61K 38/48 | (2006.01) |
| A61K 36/185 | (2006.01) |
| A23L 1/30 | (2006.01) |
| A61K 36/22 | (2006.01) |
| A61K 36/48 | (2006.01) |
| A61K 36/81 | (2006.01) |
| A61K 36/899 | (2006.01) |
| A61K 36/8998 | (2006.01) |

(52) U.S. Cl.
CPC ........... *A61K 38/4873* (2013.01); *A23L 1/3002* (2013.01); *A61K 36/185* (2013.01); *A61K 36/22* (2013.01); *A61K 36/48* (2013.01); *A61K 36/81* (2013.01); *A61K 36/899* (2013.01); *A61K 36/8998* (2013.01); *C12Y 304/22014* (2013.01)

(58) Field of Classification Search
CPC .................................................. A61K 36/185
See application file for complete search history.

(56) References Cited

U.S. PATENT DOCUMENTS

| | | | |
|---|---|---|---|
| 5,500,241 A | 3/1996 | Balasingham et al. | |
| 6,596,696 B1 * | 7/2003 | Uchida et al. | 514/27 |
| 7,862,840 B2 * | 1/2011 | Eidenberger | 424/777 |
| 8,057,831 B2 | 11/2011 | Donaldson | |
| 8,247,008 B2 | 8/2012 | Donaldson | |
| 2004/0058025 A1 | 3/2004 | Donaldson | |
| 2010/0111927 A1 | 5/2010 | Kim | |
| 2010/0143319 A1 | 6/2010 | Weir | |

FOREIGN PATENT DOCUMENTS

| | | |
|---|---|---|
| WO | WO01/70259 | 9/2001 |
| WO | WO 2008/136689 | 11/2008 |

OTHER PUBLICATIONS

Sun-Waterhouse et al. International J of Food Sciences and Nutrition, 2009, 60(s7):251-264.*
Rassam et al. Phytochemistry, 2004, 65:19-30.*
International Search Report, PCT/NZ2012/000066, Sep. 21, 2012.

* cited by examiner

*Primary Examiner* — Bin Shen
(74) *Attorney, Agent, or Firm* — Young & Thompson

(57) ABSTRACT

The present invention relates to a dietary supplement and methods of use thereof. More particularly, the invention relates to a composition including a kiwifruit extract in combination with an amylase inhibitor and/or a bifunctional protease-amylase inhibitor, particularly, but not exclusively, for managing gut health or for the treatment or prevention of digestive dysfunction, gastrointestinal disorders or symptoms thereof.

19 Claims, 3 Drawing Sheets

DIETARY SUPPLEMENT FOR MANAGING GUT HEALTH

FIELD OF THE INVENTION

The present invention relates to a dietary supplement and methods of use thereof. More particularly; the invention relates to a composition comprising a kiwifruit extract in combination with an amylase inhibitor and/or a bifunctional protease-amylase inhibitor, particularly but not exclusively, for managing gut health or for the treatment or prevention of digestive dysfunction, gastrointestinal disorders and/or symptoms thereof.

BACKGROUND

It is known that fibre is essential for healthy bowel function and a diet rich in fibre reduces the risk of a number of bowel problems. When fibre passes through the bowel it absorbs water, so it increases the bulk of the waste matter. This also makes the waste softer and increases the speed and ease with which it passes through the bowel. Fibre supplements which contain a high amount of dietary fibre and can be taken on a daily basis to aid the digestion process are known. However, known fibre formulations can be unpleasant and unpalatable to consume. Also, fibre alone is not sufficient for the complete functioning of the digestive system.

The gut microflora is also an important factor in digestive function. In humans, gut microflora comprises more than 500 different species of bacteria that have a great metabolic impact upon human health. The gut microflora can be divided into potentially deleterious and potentially health-promoting species. For example, some *Clostridium* species and proteolytic *Bacteroides* species are considered potentially harmful because of their association with certain acute and chronic gastrointestinal complaints. Their metabolic end products are toxic and can cause cellular destruction in the bowel. On the other hand, *Bifidobacterium* species and the lactic acid bacteria, particularly *Lactobacillus* species, are considered to play an important role in a healthy gut ecosystem through their antagonistic activities towards potential pathogens, immunomodulatory activities, production of short chain fatty acids and reduction of microflora associated enzyme activities involved in the production of carcinogens and genotoxins.

The consumption of food ingredients known as prebiotics can aid in treating or preventing digestive dysfunction or gastrointestinal disorders. A prebiotic is a non-digestible food ingredient that promotes the growth and/or activity of one or more bacteria in the digestive system which may beneficially affect the host, thus improving host health. Known prebiotics include dietary soluble fibres such as inulin and lactulose, which are able to survive the digestion process and selectively stimulate beneficial members of the gut microflora, such as bifidobacteria, in the colon.

Other compositions containing probiotics or prebiotics or a combination thereof are also available. Some of these compositions may have unwanted side-effects such as excessive gas production, uncomfortable bloating, or may not be tolerated by the recipient. Others are based on synthetic materials or compounds, and as such may conflict with other medications. Natural or organic products are becoming increasingly popular with consumers.

Enzymes also play a role in the digestion process. In the human gastrointestinal system, proteolytic enzymes operate by breaking down long-chain peptides or proteins into shorter chains or individual amino acids which can then pass into the cells lining the small intestine. These more simple compounds may be used for growth and maintenance of the body or be converted to energy. Some vitamins present in foods are only made available to be absorbed by the gastrointestinal lining once the material surrounding them is broken down. For example, much of the vitamin B 12 in red meat would be unavailable if the proteinaceous matrix was not first hydrolysed.

Typically, the human body produces most but not all of the enzymes it requires for efficient digestion. Some disorders, diets or lifestyles can also result in the deficiency of certain enzymes. Such enzymes can be supplemented by the food we eat or through the use of dietary supplements, for example. However, the body may produce digestive compounds (such as proteolytic enzymes in saliva and the gut and the low pH stomach acids) that inhibit or break down the beneficial enzymes, making it difficult for the body to obtain the full balance of enzymes required for efficient digestion. The presence of these digestive compounds is a problem when trying to maintain or improve digestive function by oral administration of pharmaceuticals, dietary supplements or other beneficial biological products such as prebiotic enzymes, as it reduces efficacy.

*Actinidia*, a genus of plants cultivated mainly for its fruit (kiwifruit), grows in various countries. The constituent cysteine protease of the fruit, actinidin, is an enzyme shown to enhance gastric protein digestion in vitro (Reid, 2004). Zyactinase® is a freeze dried powder derived from kiwifruit, containing the enzyme, actinidin, plant polyphenols, dietary fiber, carbohydrates, and oligosaccharides including galactoglucomannan, a type of oligosaccharide, which has been isolated from kiwifruit (Schroder et al, 2001).

Kiwifruit has a high density of vitamin C, vitamin E, potassium and magnesium salts, and is also an excellent source of dietary fibre. It is also low in fat, contains no cholesterol, has a high antioxidant potential and is particularly high in two amino acids: arginine and glutamate. Compositions comprising kiwifruit extract from fruit of the species *Actinidia deliciosa* have been shown to have a prebiotic effect and to comprise fibre and enzymes. Such extracts provide benefits in respect of the health of the digestive system and the treatment and prevention of digestive dysfunction and/or gastrointestinal disorders (PCT/NZ2008/000098).

Previous compositions comprising kiwifruit extract have been formulated in capsule form for oral ingestion. This has the benefit that digestive enzymes cannot act on the extract until the soft gelatine case has been broken down in the stomach. However, other formulations for oral delivery are desirable as capsules may have a number of drawbacks. These drawbacks include:

Flavour—capsules do not allow a flavour component to be effectively added to the composition.

Palatability and convenience—a number of consumers dislike having to take capsules or find it difficult to swallow capsules. Taste and problems with swallowing the capsules are particularly important considerations when providing formulations suitable for children.

Cost—many pharmaceutical and nutraceutical companies do not have the equipment necessary to fill soft capsules and have to transport the compositions to have them processed, adding to the cost. This cost can increase the price the consumer pays.

Moisture—soft capsules are extremely water soluble, which helps them to dissolve in the body. However, this means that soft capsules are very sensitive to heat and humidity. In hot or humid climates, capsules may stick together or even break open before use.

Dietary Restrictions—soft capsules may be made out of gelatine which is traditionally made out of animal material. Many groups, such as vegetarians, have dietary proscriptions that prevent them from consuming these animal products. Gelatine capsules may also violate the religious dietary restrictions of observant Jews, Muslims, Buddhists and Hindus.

Dosage—the dosage able to be delivered in a particular volume of capsule is often less than that possible with other dosage forms. This effectively reduces the efficacy of a single capsule dosage in comparison to these other forms, requiring more capsules to be taken to achieve an effective dose. This may be inconvenient and difficult for the person taking a dietary supplement, resulting in the person not being able to comply with a particular treatment regime.

It is an object of the invention to provide one or more compositions and/or uses that overcome or ameliorate at least one of the disadvantages of the prior art or at least to provide the public with a useful choice.

SUMMARY OF THE INVENTION

The inventors have conducted extensive research and have formulated a composition which may address a number of the problems noted above. During this research, the inventors found that when a kiwifruit extract is exposed to digestive enzymes, particularly those present in the mouth, such as amylase, the activity of the beneficial enzyme(s) in the extract is reduced and therefore the efficacy of the composition in the gut is also likely to be compromised. The composition devised by the inventors may be exposed to digestive enzymes while still retaining a desired level of enzyme activity and beneficial function in the gut.

In a first aspect, the invention provides a composition comprising a kiwifruit extract in combination with an amylase inhibitor and/or a bifunctional protease-amylase inhibitor, the composition also optionally comprising one or more suitable diluents, carriers and/or excipients.

In one embodiment, the kiwifruit extract comprises at least one cysteine protease enzyme.

In one embodiment, the at least one cysteine protease enzyme comprises actinidin.

In one embodiment, the kiwifruit extract comprises actinidin with an enzyme activity of substantially 1500 U/g to substantially 6000 U/g, in one embodiment substantially 3000 U/g to 5000 U/g.

In one embodiment, the kiwifruit extract comprises at least one cysteine protease enzyme as well as fibre and/or a prebiotic component.

In one embodiment, the kiwifruit extract is derived by a method of extraction as described in WO 2008/1366899.

In one embodiment, the kiwifruit extract has the defining characteristics of the kiwifruit extract described in and the subject of WO 2008/1366899, NZ554991 or U.S. Pat. No. 8,057,831.

In one embodiment, the kiwifruit extract has the defining characteristics of a kiwifruit enzyme complex with the brand name Zyactinase®, and more preferably Zyactinase® 45.

In one embodiment, the kiwifruit extract is a kiwifruit enzyme complex with the brand name Zyactinase®, and more preferably Zyactinase® 45.

In one embodiment, the amylase inhibitor and/or bifunctional protease-amylase inhibitor is as hereinafter described.

In one particular embodiment, the amylase inhibitor and/or bifunctional protease-amylase inhibitor is extracted from white kidney bean. In one embodiment, the amylase inhibitor and/or the bifunctional protease-amylase inhibitor is provided as a white kidney bean extract.

In one particular embodiment, the extract from white kidney bean has the defining characteristics of StarchLite®.

In one particular embodiment, the extract from white kidney bean is StarchLite®.

In one embodiment, the amylase inhibitor and/or the bifunctional protease-amylase inhibitor is present in the composition at a minimum concentration of approximately 0.5% (w/w) and at a maximum concentration of approximately 50% (w/w), approximately 40%, approximately 30%, approximately 20%, approximately 10%, approximately 5%, approximately 2%, or approximately 1%.

In one embodiment, the kiwifruit extract is present in the composition at a maximum concentration of approximately 99.5% and at a minimum concentration of approximately 50%, approximately 60%, approximately 70%, approximately 80%, approximately 90%, approximately 95%, approximately 98%, or approximately 99%.

The ratio of kiwifruit extract:amylase inhibitor and/or bifunctional protease-amylase inhibitor in certain embodiments is between approximately 200:1 and 1:1, approximately 99:1 and 1:1, approximately 49:1 and 1:1, approximately 35:1 and 1:1, approximately 30:1 and 1:1, approximately 28:1 and 1:1, approximately 19:1 and 1:1, approximately 10:1 and 1:1, approximately 9:1 and 1:1, approximately 4:1 and 1:1 or is approximately 1:1.

In other embodiments, the ratio of kiwifruit extract:amylase inhibitor and/or bifunctional protease-amylase inhibitor is approximately 34.9:1, approximately 27.5:1 or approximately 9.6:1, In certain particular embodiments, the composition comprises kiwifruit extract at a concentration of approximately 98 to 99.5% (w/w) and amylase inhibitor at approximately 0.5 to 2.0% (w/w), or kiwifruit extract at approximately 98.5 to 99.5% and amylase inhibitor at approximately 0.5 to 1.5% (w/w), or kiwifruit extract at approximately 98 to 99% and amylase inhibitor at approximately 1.0 to 2.0% (w/w), or kiwifruit extract at approximately 99% and amylase inhibitor at approximately 1%.

In certain particular embodiments the composition comprises:
a) kiwifruit extract at a concentration of approximately 97.5 to 99.5% (w/w) and
b) a bifunctional protease-amylase inhibitor at a concentration of approximately 0.5 to 2.5% (w/w); or
a) kiwifruit extract at a concentration of approximately 98 to 99.5% (w/w) and
b) a bifunctional protease-amylase inhibitor or at a concentration of approximately 0.5 to 2.0% (w/w); or
a) kiwifruit extract at approximately 98.5 to 99.5% and
b) a bifunctional protease-amylase inhibitor at a concentration of approximately 0.5 to 1.5% (w/w); or
a) kiwifruit extract at approximately 98 to 99% and
b) a bifunctional protease-amylase inhibitor at a concentration of approximately 1.0 to 2.0% (w/w); or
a) kiwifruit extract at approximately 99% and
b) a bifunctional protease-amylase inhibitor at a concentration of approximately 1%.

In other particular embodiments, the amylase inhibitor is present in the composition at approximately 1.98% (w/w) and the kiwifruit extract is present at approximately 69.15%, the amylase inhibitor is present in the composition at approximately 2% (w/w) and the kiwifruit extract is present at approximately 55%, or the amylase inhibitor is present in the composition at approximately 1.6% (w/w) and the kiwifruit extract is present at approximately 15.38%.

In one particular embodiment, the composition comprises
a) a bifunctional protease-amylase inhibitor at a concentration of approximately 1.98% (w/w) and
b) kiwifruit extract at approximately 69.15%;
or
a) a bifunctional protease-amylase inhibitor at a concentration of approximately 2% (w/w) and
b) kiwifruit extract at approximately 55%;
or
a) a bifunctional protease-amylase inhibitor at a concentration of approximately 1.6% (w/w) and
b) kiwifruit extract at approximately 15.38%.

In other particular embodiments, the suitable diluents, carriers and/or excipients may be selected from the group comprising tableting sugar (for example Di-Pac® tableting sugar from Domino Specialty Ingredients, Florida USA), tropical flavour, natural intense sweetener, magnesium stearate, silicon dioxide, evaporated cane juice, rice syrup/rice syrup solids, fructose, sunflower lecithin, natural flavors, corn starch, glycerin, sunflower oil, natural colour from chlorophyll, tableting sugar, apple powder, citric acid, lemon powder, sucralose, copper chlorophyllin, tropical flavour powder, natural kiwi/strawberry flavour with natural antioxidants, sodium copper chlorophyllin.

In one embodiment, the composition is formulated in a form selected from the group consisting of tablet form, chewable tablet form, soft chew form, powder form, powder form for suspension in a liquid, capsule form, liquid form or soft gel form.

In one particular embodiment, the composition is formulated as a tablet and the suitable diluents, carriers and/or excipients may be selected from the group comprising tableting sugar, tropical flavour, natural sweetener, magnesium stearate and silicon dioxide.

In one particular embodiment, the composition is formulated as a powder for suspension in a liquid and the suitable diluents, carriers and/or excipients may be selected from the group comprising apple powder, citric acid, fructose, lemon powder, sucralose, copper chlorophyllin and tropical flavour powder.

In one particular embodiment, the composition is formulated as a soft chew and the suitable diluents, carriers and/or excipients may be selected from the group comprising evaporated cane juice, fructose, natural kiwi/strawberry flavour with natural antioxidants, sodium copper chlorophyllin, glycerine, rice syrup/rice syrup solids, sunflower lecithin/sunflower oil.

In one particular embodiment, the composition is formulated as a tablet and the amylase inhibitor is present in the composition at approximately 1.98% (w/w) and the kiwifruit extract is present at approximately 69.15%.

In one particular embodiment, the composition is formulated as a tablet and the composition comprises
a) a bifunctional protease-amylase inhibitor at a concentration of approximately 1.98% (w/w) and
b) kiwifruit extract at approximately 69.15%.

In one particular embodiment, the composition is formulated as a powder for suspension in a liquid and the amylase inhibitor is present in the composition at approximately 2% (w/w) and the kiwifruit extract is present at approximately 55%.

In one particular embodiment, the composition is formulated as a powder for suspension in a liquid and the composition comprises
a) a bifunctional protease-amylase inhibitor at a concentration of approximately 2% (w/w) and
b) kiwifruit extract at approximately 55%.

In one particular embodiment, the composition is formulated as a soft chew and the amylase inhibitor is present in the composition at approximately 1.6% (w/w) and the kiwifruit extract is present at approximately 15.38%.

In one particular embodiment, the composition is formulated as a soft chew and the composition comprises
a) a bifunctional protease-amylase inhibitor at a concentration of approximately 1.6% (w/w) and
b) kiwifruit extract at approximately 15.38%.

In a second aspect, the invention provides a method of treating or preventing digestive dysfunction, a gastrointestinal disorder, and/or one or more symptoms associated with a digestive disorder or a gastrointestinal disorder comprising administering to a subject a composition as described in the first aspect.

In one embodiment, the digestive dysfunction or gastrointestinal disorder is selected from the group comprising constipation, an inflammatory bowel condition, indigestion, gastric reflux, bloating, gas, abdominal pain, diarrhoea, heartburn, irritable bowel syndrome, or one or more symptoms associated with any of these conditions.

In a third aspect, the invention provides a method of altering, maintaining and/or restoring a balance of intestinal microflora of a subject comprising administering to the subject a composition as described in the first aspect.

In one embodiment, the intestinal microflora is intestinal bacteria and the balance is altered to promote the amount, growth or efficacy of beneficial bacteria.

In particular embodiments, the beneficial bacteria are selected from the group comprising probiotic bacteria.

In further particular embodiments, the beneficial bacteria are selected from the group comprising bifidobacteria and lactobacilli.

In further particular embodiments the beneficial bacteria are selected from the group consisting of *Lactobacillus reuteri, Lactobacillus acidophilus, Pediococcus acidilactici,* and *Lactobacillus plantarum.*

In one embodiment, intestinal microflora is intestinal bacteria and the balance is altered to reduce the amount, growth or efficacy of pathogenic gut bacteria.

In one embodiment the pathogenic gut bacteria are selected from the group comprising *Bacteroides, Clostridia,* coliforms, and sulphate reducing bacteria. Some examples include *Escherichia coli, E. coli* 0157:H7, *Salmonella typhimurium,* and *Staphylococcus aureus.*

In a fourth aspect, the invention provides a method of maintaining and/or improving gastrointestinal health comprising administering to a subject a composition as described in the first aspect.

In a particular embodiment, the gastrointestinal health of a subject is maintained and/or improved by the prevention or treatment of any one of the digestive dysfunctions, gastrointestinal disorders, and/or one or more symptoms thereof described in the fifth aspect and/or one or more of the following:
 a. an increase in spontaneous bowel movements
 b. an increase in complete spontaneous bowel movements
 c. a decrease in abdominal discomfort or pain
 d. a decrease in flatulence
 e. a decrease in bowel urgency
 f. a decrease in wind or burping
 g. a decrease in bloating In a fifth aspect, the invention provides the use of a composition according to the first aspect in the manufacture of a medicament for treating or preventing digestive dysfunction, a gastrointestinal disorder, and/or one or more symptoms associated with a digestive dysfunction or gastrointestinal disorder.

In one embodiment, the digestive dysfunction or gastrointestinal disorder is selected from the group comprising constipation, an inflammatory bowel condition, indigestion, gastric reflux, bloating, gas, abdominal pain, diarrhoea, heartburn, irritable bowel syndrome, or one or more symptoms associated with any of these conditions.

In a sixth aspect, the invention provides the use of a composition according to the first aspect in the manufacture of a medicament for altering, maintaining and/or restoring a balance of intestinal microflora of a subject.

In one embodiment, the microflora is intestinal bacteria and the balance is altered to promote the amount, growth or efficacy of beneficial bacteria.

In particular embodiments, the beneficial bacteria are selected from the group comprising probiotic bacteria.

In further particular embodiments, the beneficial bacteria are selected from the group comprising bifidobacteria and lactobacilli.

In further particular embodiments the beneficial bacteria are selected from the group consisting of *Lactobacillus reuteri, Lactobacillus acidophilus, Pediococcus acidilactici*, and *Lactobacillus plantarum*.

In one embodiment, the balance of intestinal bacteria is altered to reduce the amount, growth or efficacy of pathogenic gut bacteria.

In one embodiment, the pathogenic gut bacteria are selected from the group comprising *Bacteroides, Clostridia,* coliforms, and sulphate reducing bacteria. Some examples include *Escherichia coli, E. coli* 0157:H7, *Salmonella typhimurium*, and *Staphylococcus aureus*.

In a seventh aspect, the invention provides the use of a composition according to the first aspect in the manufacture of a medicament for maintaining and/or improving gastrointestinal health.

In a particular embodiment, the gastrointestinal health of a subject is maintained and/or improved by the prevention or treatment of any one of the digestive dysfunctions, gastrointestinal disorders, and/or one or more symptoms thereof described in the fifth aspect or one or more of the following:
 a. an increase in spontaneous bowel movements
 b. an increase in complete spontaneous bowel movements
 c. a decrease in abdominal discomfort or pain
 d. a decrease in flatulence
 e. a decrease in bowel urgency
 f. a decrease in wind or burping
 g. a decrease in bloating The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

DETAILED DESCRIPTION OF THE INVENTION

Figure 1:
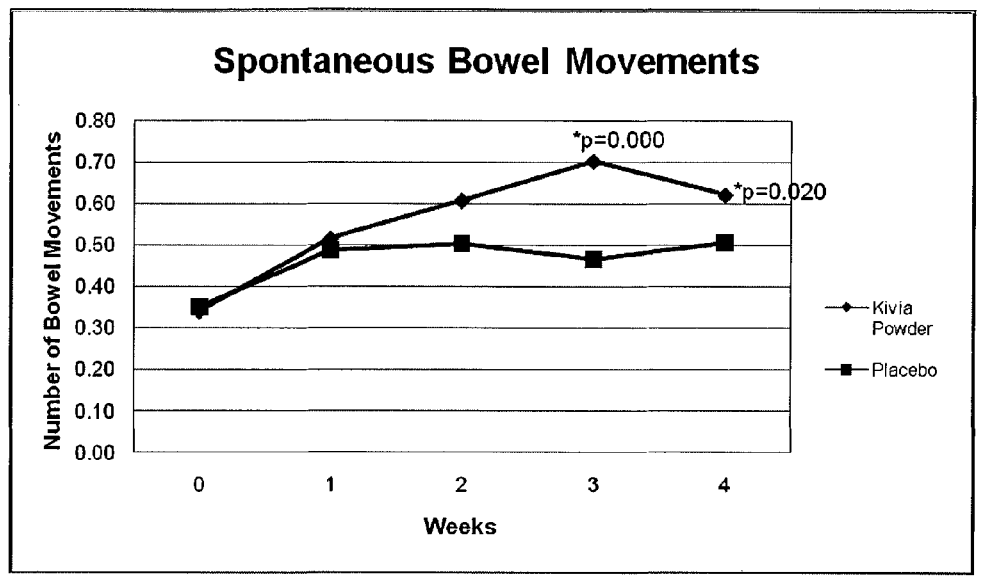
FIG. 1 shows the number of spontaneous bowel movements over a four week trial of a composition of the invention.

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

As used herein, the terms "treatment" or "treat", or similar, are to be considered in their broadest context. The terms do not necessarily imply that a subject is treated until total recovery. Accordingly, these terms include the amelioration of the symptoms or severity of a particular condition or preventing or otherwise reducing the risk of developing a particular condition.

A "subject" as referred to herein refers to any animal, preferably mammals and including humans.

"Prebiotic material" refers to any non-digestible components of the kiwifruit extract that beneficially affect the host by selectively promoting the growth and/or activity of one or more health promoting microflora, for example bacteria, in the gut.

A "bifunctional protease-amylase inhibitor" as referred to herein is any compound, extract or composition that has the dual function of being able to at least suppress or retard the function or activity of one or more amylase and one or more protease enzymes. It will be understood by one of skill in the art that the suppression or retardation of the function or activity of a protease may occur at the same time or at a different time to the suppression or retardation of the function or activity of an amylase. The bifunctional function of the inhibitor may be the result of a single compound or two or more compounds in an extract or composition. Use of the term "inhibitor" should not be taken to imply that an amylase and/or protease is completely inhibited, although this may be preferred.

"Symptoms associated with a digestive disorder or a gastrointestinal disorder" should be taken to include abdominal discomfort or pain, flatulence, bowel urgency, wind or burping, bloating, alteration of bowel habits, constipation, diarrhea, reduced bowel movements, feeling of incomplete evacuation, anal burning, hard stools and heartburn for example. Throughout the specification, unless the context requires otherwise, percentages provided are percentage w/w.

A number of different compounds were tested in conjunction with a kiwifruit extract to determine whether they affected the enzyme activity of the kiwifruit extract, which could affect the ability of the extract to maintain a healthy gastrointestinal tract. During this research, the inventors found that eating kiwifruit did not have the same beneficial effects as consuming an encapsulated kiwifruit extract. In light of this, they hypothesised that one or more salivary enzymes were reducing the efficacy of the beneficial enzymes prior to reaching the stomach. Saliva contains a number of enzymes that could have been causing this effect including α-amylase (EC3.2.1.1), lingual lipase, lysozyme, salivary lactoperoxidase, lactoferrin, immunoglobulin A, salivary acid phosphatases A+B, N-acetylmuramoyl-L-alanine amidase, NAD(P)H dehydrogenase (quinone), superoxide dismutase, glutathione transferase, class 3 aldehyde dehydrogenase, glucose-6-phosphate isomerise and tissue kallikrein (Boron, 2008).

Analysis of the kiwifruit extract showed that it contained three main components found to act synergistically in providing beneficial health effects: soluble fibre, a pre-biotic component and one or more cysteine protease enzymes.

Capsule dosage forms are effective in shielding the extract from salivary enzymes that the inventors have shown degrade the beneficial enzymes and reduce overall therapeutic efficacy. However, as noted previously, dosage forms other than capsules may be desirable.

Tests of kiwifruit extract (example 3) in the presence of saliva showed that a white bean extract increased the kiwifruit extract enzyme activity. The inventors contemplate that the finding may be explained by a protective function of the white bean extract from the salivary amylase and/or salivary protease present. White bean extract contains an effective amylase inhibitor which the inventors believe may prevent the breakdown of the pre-biotic component by the action of salivary amylase.

Further to the above effect, the inventors surprisingly found that white bean extract also enhanced the activity of enzyme(s) in the kiwifruit extract in the absence of saliva (see examples 1 and 2). Further, the inventors found that compositions of the invention have a high stability.

Without wishing to be bound by theory, the inventors believe that these surprising effects can be explained if the white bean extract contains bifunctional enzymatic activity as both a protease inhibitor and an amylase inhibitor. Protease inhibitors such as serine protease inhibitors exhibit some structural homology to cysteine proteases which are found in the kiwifruit extract. It is hypothesised that in the absence of the white bean extract, cysteine protease activity breaks down components of the kiwifruit extract enzyme complex and other components and reduces its efficacy and activity. The inventors believe that with white bean extract present, the serine protease inhibitor binds loosely to the cysteine protease temporarily inhibiting the cysteine protease activity resulting in greater stability of the kiwifruit enzyme complex and consequently a longer shelf life. When the kiwifruit extract is formulated as a capsule on its own without white bean extract, the one or more cysteine proteases in the kiwifruit extract may break down the capsule and the other components of Zyactinase® resulting in a reduced shelf life.

In addition, the inventors contemplate that the increased enzyme activity of the kiwifruit extract may be explained by the detachment of the loosely bound serine protease inhibitor in white bean extract from the cysteine protease in the kiwifruit extract due to the lower pH on entering the stomach (as simulated during the enzyme assays in examples 1 to 3). The inventors believe this causes a change in the active binding site of the enzyme complex which in turn modifies the reaction mechanism and therefore alters the activation energy of the reaction resulting in an increased kiwifruit extract enzyme complex efficacy and activity.

While the inventors have demonstrated the effects using a white bean extract, it is envisaged that any amylase inhibitor and/or a bifunctional protease-amylase inhibitor when provided either together or individually would have similar effects and is within the scope of the invention.

The present invention goes at least some way towards addressing the problem of inhibition or breakdown of beneficial enzymes in the kiwifruit extract prior to or during passage into the gastrointestinal tract, and further, enhances the enzymatic activity of the kiwifruit extract.

The invention provides a composition comprising a kiwifruit extract in combination with an amylase inhibitor and/or a bifunctional protease-amylase inhibitor wherein the composition may also further comprise one or more suitable diluents, carriers and/or excipients.

"Kiwifruit extract" as referred to herein is an extract from the whole fruit of a kiwifruit comprising at least one cysteine protease enzyme. In one embodiment, the at least one cysteine protease enzyme comprises actinidin. In one embodiment, the kiwifruit extract comprises actinidin with an enzyme activity of substantially 1500 U/g to substantially 6000 U/g, preferably substantially 3000 U/g to 5000 U/g when measured using the Vital Foods method as described in example 2 herein. In one embodiment, the kiwifruit extract comprises one or more cysteine protease enzymes, fibre and a pre-biotic component. While there are beneficial effects of these components, it may also be desirable to remove the fibre component and/or a pre-biotic component and it is contemplated that the kiwifruit extract may comprise any one or more of these in addition to at least one cysteine protease enzymes. In one embodiment, the extract is derived from a kiwifruit in the *Actinidia* family or a hybrid thereof. In a particular embodiment, the kiwifruit is of the species *Actinidia deliciosa* (formerly classified as *Actinidia chinensis*), *Actinidia chinensis, Actinidia arguta* or a hybrid derived from one or more of these species.

In a further embodiment, compositions of the invention comprise kiwifruit extract that has been processed to include an additional, increased or decreased proportion of one or more components. For example such components may include: kiwifruit derived enzymes, fibre or pre-biotic components; components, such as enzymes, derived from different extracts including plant and bacterial extracts; pro-biotic bacteria (examples of which are defined herein); additional synthetically produced components including enzymes.

In one embodiment, the kiwifruit extract referred to herein is an extract prepared from the kiwifruit pulp (i.e. kiwifruit without the seeds or skin). In a further embodiment, the kiwifruit extract is prepared according to the method(s) set out in WO2008/136689 or WO2006/118476. In one embodiment, the kiwifruit extract has the defining characteristics of the kiwifruit extract described in and the subject of WO2008/136689 or WO2006/118476. In an alternative embodiment, the kiwifruit extract has the defining characteristics of a kiwifruit enzyme complex with the brand name Zyactinase®, and more preferably Zyactinase® 45. In a particular embodiment, the kiwifruit extract is the kiwifruit enzyme complex with the brand name Zyactinase®, and more preferably Zyactinase® 45. Zyactinase® is the primary active ingredient present in Phloe® capsules produced by and available from Vital Food Processors Limited, New Zealand.

While the experiments and preferred ratios of compositions defined herein use kiwifruit extract extracted according the method described above, it should be appreciated that kiwifruit extracts extracted according to other methods are also encompassed within the invention.

In broad terms, an "amylase inhibitor" is a compound, extract or composition that results in at least some suppression or retardation of the function or activity of one or more amylase enzymes. Use of the term "inhibitor" should not be taken to imply that the amylase activity is completely inhibited, although this may be preferred. In one embodiment, the amylase inhibitor is a protein. Amylase inhibitors may also be identified by their action in suppressing the activity of α-amylase for example by methods described in Rakhimova et al. (2008), Sharma and Gupta (2001) and Mosolov et al. (2001).

Several studies have shown that amylase inhibitors are effective in reducing starch digestion in all parts of the gastrointestinal tract (reviewed in Obiro, Zhang and Jiang (2008)). This research indicates that an amylase inhibitor is active against salivary and pancreatic amylases throughout the gastrointestinal tract. Accordingly, the inventors contemplate the invention also being applicable to encapsulated kiwifruit extract that is released in the stomach or further along the gastrointestinal tract.

Skilled persons will readily appreciate amylase inhibitors of use in the invention. However, by way of example only, amylase inhibitors can be extracted from several types of plants, especially those in the legume family. Currently available α-amylase inhibitors are commonly extracted from either white kidney bean (*Phaseolus vulgaris*) or wheat (*Triticum aestivum*) although they can also be found in *Lens culinaris, Psophocarpus tetragonolobus, Cicer arietinum, Vigna aconitifolia*, oats, sorghum, rye, barley, mango seeds, kiwifruit seeds and potatoes. An example of a commercial preparation of amylase inhibitor is StarchLite® (page 7, Obiro, Zhang and Jiang (2008)) produced by PharmaChem Laboratories Inc., New Jersey. This preparation has "Generally Recognised As Safe" (GRAS) status by the United States Food and Drug Administration under sections 201(s) and 409 of the Federal Food, Drug, and Cosmetic Act.

While amylase inhibitors have been used in weight loss products, they have not previously been used or postulated as being effective for the enhancement of the efficacy of kiwifruit extracts for managing gut health or for the treatment or prevention of a variety of gastrointestinal disorders.

As mentioned hereinbefore, the invention may be performed using a bifunctional protease-amylase inhibitor. In one embodiment it is a serine protease-amylase inhibitor; or a trypsin-amylase inhibitor. "Bifunctional protease-amylase inhibitors" are defined hereinbefore and can include any suitable compound, extract or composition having a protease-amylase inhibitory activity.

Skilled persons will readily appreciate bifunctional protease-amylase inhibitors of use in the invention. However, by way of example only, they may be extracted from several types of plants, especially those in the legume family, from white kidney bean (*Phaseolus vulgaris*) wheat (*Triticum aestivum*), *Lens culinaris, Psophocarpus tetragonolobus, Cicer arietinum, Vigna aconitifolia*, oats, sorghum, rye, barley, mango seeds, kiwifruit seeds and potatoes.

Bifunctional protease-amylase inhibitors may be identified by their action in suppressing the activity of trypsin and α-amylase for example by methods described in Rakhimova et al. (2008), Sharma and Gupta (2001) and Mosolov et al. (2001).

In one embodiment, the bifunctional protease-amylase inhibitor is white bean extract, in one particular embodiment it is a white bean extract having the defining characteristics of Starchlite®. In one particular embodiment, it is Starchlite®

As used herein, the phrase "suitable diluents, carriers and/or excipients" is intended to include substances that are useful in preparing a composition, may be co-administered with composition of the invention while allowing it to perform its intended function, and are generally safe, non-toxic and neither biologically nor otherwise undesirable. Suitable diluents, carriers and/or excipients include those suitable for veterinary use as well as human use. Examples of suitable diluents, carriers and/or excipients include solutions, solvents, dispersion media, delay agents, emulsions and the like.

Those of ordinary skill in the art will readily appreciate a variety of suitable diluents, carriers and/or excipients which may be employed in compositions of the invention. However, by way of example, suitable diluents, carriers and/or excipients for use may be selected from the group comprising tableting sugar (for example Di-Pac® tableting sugar from Domino Specialty Ingredients, Florida USA), tropical flavour, natural intense sweetener, magnesium stearate, silicon dioxide, evaporated cane juice, rice syrup/rice syrup solids, fructose, sunflower lecithin, natural flavors, corn starch, glycerin, sunflower oil, natural colour from chlorophyll, tableting sugar, apple powder, citric acid, lemon powder, sucralose, copper chlorophyllin, tropical flavour powder, natural kiwi/strawberry flavour with natural antioxidants, sodium copper chlorophyllin.

Examples of suitable diluents, carriers and/or excipients for use in tablet form include tableting sugar (for example Di-Pac® tableting sugar from Domino Specialty Ingredients, Florida USA), tropical flavour, natural intense sweetener, magnesium stearate and silicon dioxide.

Examples of suitable diluents, carriers and/or excipients for use in soft chew form include evaporated cane juice, rice syrup, fructose, sunflower lecithin, natural flavors, corn starch, glycerin, sunflower oil and natural color from chlorophyll.

Examples of suitable diluents, carriers and/or excipients for use in capsule form include isomalt, magnesium stearate, silicon dioxide.

Examples of suitable diluents, carriers and/or excipients for use in powder for suspension in a liquid form include apple powder, citric Acid, lyophilized lemon, fructose, sucralose, copper chlorophyll and tropical flavour.

Additionally, it is contemplated that a composition in accordance with the invention may be formulated with one or more additional ingredients, including for example colouring agents, flavouring agents or active ingredients which may be of benefit to a subject in particular instances.

Ingredients identified in accordance with this embodiment of the invention may be formulated with one or more suitable carriers, diluents and/or excipients, according to standard procedures as would be known and understood by one of skill in the art, having regard to the desired dosage form. It should be understood that the process used to produce the formulation should minimise heating or other steps that may denature the active enzymes in the composition. Exemplary methods that may be used to produce a soft chew formulation are described in U.S. Pat. Nos. 6,517,886 and 6,482,465.

Further embodiments of the invention may contain extracts made into liquid compositions, or included in foodstuffs and beverages. For example, the compositions of the present invention may be incorporated in frozen or chilled desserts; blended with sugar or prepared as a sprinkle on product for use on breakfast cereals and fruit; incorporated into a wide variety of drinks and beverages; blended with milk or cream; blended with yoghurt, or ice cream; encapsulated and administered orally or as a suppository; pressed into tablet form to be administered orally or formed into a drench for oral administration.

The optimal amount of kiwifruit extract, bifunctional compound and/or amylase inhibitor present in the composition may differ according to the particular dosage form and the unit dosage required.

In one embodiment, the amylase inhibitor and/or bifunctional protease-amylase inhibitor is present in the composition at a minimum concentration of 0.5% (w/w) and at a maximum concentration of approximately 50%, approximately 40%, approximately 30%, approximately 20%, approximately 10%, approximately 5%, approximately 2%, or approximately 1%.

In one embodiment, the kiwifruit extract is present in the composition in a maximum concentration of approximately 99.5% and at minimum concentration of approximately 50%, approximately 60%, approximately 70%, approximately 80%, approximately 90%, approximately 95%, approximately 98%, or approximately 99%.

In one particular embodiment the composition comprises kiwifruit extract at a concentration of approximately 98 to 99.5% (w/w) and amylase inhibitor at approximately 0.5 to 2.0% (w/w), or kiwifruit extract at approximately 98.5 to 99.5% and amylase inhibitor at approximately 0.5 to 1.5% (w/w), or kiwifruit extract at approximately 98 to 99% and amylase inhibitor at approximately 1.0 to 2.0% (w/w), or kiwifruit extract at approximately 99% and amylase inhibitor at approximately 1%.

In one particular embodiment the composition comprises:
a) kiwifruit extract at a concentration of approximately 97.5 to 99.5% (w/w) and
b) a bifunctional protease-amylase inhibitor at a concentration of approximately 0.5 to 2.5% (w/w); or
a) kiwifruit extract at a concentration of approximately 98 to 99.5% (w/w) and
b) a bifunctional protease-amylase inhibitor at a concentration of approximately 0.5 to 2.0% (w/w); or
a) kiwifruit extract at approximately 98.5 to 99.5% and
b) a bifunctional protease-amylase inhibitor at a concentration of approximately 0.5 to 1.5% (w/w); or
a) kiwifruit extract at approximately 98 to 99% and
b) a bifunctional protease-amylase inhibitor at a concentration of approximately 1.0 to 2.0% (w/w); or
a) kiwifruit extract at approximately 99% and
b) a bifunctional protease-amylase inhibitor at a concentration of approximately 1%.

The ratio of kiwifruit extract:amylase inhibitor and/or bifunctional protease-amylase inhibitor in certain embodiments is between approximately 200:1 and 1:1, approximately 99:1 and 1:1, approximately 49:1 and 1:1, approximately 35:1 and 1:1, approximately 30:1 and 1:1, approximately 28:1 and 1:1, approximately 19:1 and 1:1, approximately 10:1 and 1:1, approximately 9:1 and 1:1, approximately 4:1 and 1:1 or is approximately 1:1.

In other embodiments, the ratio of kiwifruit extract:amylase inhibitor and/or bifunctional protease-amylase inhibitor is approximately 34.9:1, approximately 27.5:1 or approximately 9.6:1.

In one particular embodiment, the amylase inhibitor is present in the composition at approximately 1.98% (w/w) and the kiwifruit extract is present at approximately 69.15%, the amylase inhibitor is present in the composition at approximately 2% (w/w) and the kiwifruit extract is present at approximately 55%, or the amylase inhibitor is present in the composition at approximately 1.6% (w/w) and the kiwifruit extract is present at approximately 15.38%.

In one particular embodiment, the composition comprises
a) a bifunctional protease-amylase inhibitor at a concentration of approximately 1.98% (w/w) and
b) kiwifruit extract at approximately 69.15%;
or
a) a bifunctional protease-amylase inhibitor at a concentration of approximately 2% (w/w) and
b) kiwifruit extract at approximately 55%;
or
a) a bifunctional protease-amylase inhibitor at a concentration of approximately 1.6% (w/w)
and
b) kiwifruit extract at approximately 15.38%.

Kiwifruit extract is effective in the treatment or prevention of digestive dysfunction, gastrointestinal disorders, and/or one or more symptoms thereof. Kiwifruit extract is of particular use in treating constipation. The prebiotic material present in kiwifruit extract can influence the balance of gastrointestinal bacteria, with a preferential promotion of the growth of beneficial bacteria and concomitant reduction in the growth of harmful bacteria (PCT/NZ2008/000098). Kiwifruit extract also has use in the maintenance or improvement of gastrointestinal health.

The present invention provides an improved composition that may be used: to treat or prevent digestive dysfunction, gastrointestinal disorders, and/or one or more symptoms thereof; for altering, maintaining and/or restoring a balance of intestinal microflora of a subject; in maintaining and/or improving the gastrointestinal health of a subject. The activity of enzymes in the kiwifruit extract is enhanced and the effect of salivary and pancreatic substances that limit the enzyme activity of the extract is reduced. These effects result in a composition with increased efficacy for the above uses when compared to the efficacy of known compositions.

The digestive dysfunction and/or gastrointestinal disorders that the invention may be used to treat includes, but is not limited to constipation, inflammatory bowel conditions, indigestion, gastric reflux, bloating, gas, abdominal pain, diarrhoea, heart-burn, irritable bowel syndrome, or symptoms associated with any of these conditions.

Maintaining and/or improving the gastrointestinal health of a subject could involve the prevention or treatment of any one of the digestive dysfunctions, gastrointestinal disorders, and/or symptoms thereof noted hereinbefore and could also involve promoting one or more of the following:
  a. an increase in spontaneous bowel movements
  b. an increase in complete spontaneous bowel movements
  c. a decrease in abdominal discomfort or pain
  d. a decrease in flatulence
  e. a decrease in bowel urgency
  f. a decrease in wind or burping
  g. a decrease in bloating According to the American Gastroenterological Association, among healthy people the frequency of bowel movements may vary from three movements a day to three per week. Constipation may be suspected if there is difficulty or pain when passing a hardened stool or if greater than three clays pass between bowel movements. Contributing factors to constipation include:
  Gender (being female)
  Age (being older)
  Diet
  Lifestyle choices
  Use of certain medications
  Bowel habits Irritable bowel syndrome (IBS) is a symptom-based diagnosis characterized by chronic abdominal pain, discomfort, bloating, and alteration of bowel habits. As a functional bowel disorder, IBS has no known organic cause. Constipation or diarrhea may also occur with either being dominant, or they may alternate. Although there is no cure for IBS, there are treatments that attempt to relieve symptoms, including dietary adjustments, medication and psychological interventions.

IBS occurs when the bowel becomes irritated and results in spasms causing abdominal pain. Constipation results in reduced bowel movements, feeling of incomplete evacuation, anal burning and hard stools. Prolonged constipation particularly with prolonged use of laxatives can over time result in inflammation leading to IBS. IBS can also result from damage during gastro infections, which is why the prebiotic component of Zyactinase® helps relieve IBS by promoting growth of beneficial bacteria.

The key difference between constipation and IBS is the presence of abdominal pain. In the clinical trial results (example 7), abdominal pain was measured and it was shown that a composition of the invention had a clinically significant effect in relieving abdominal pain. Abdominal pain is often caused as a result of gas and bloating therefore the results of the study indicate that these aspects were also treated. Additionally, flatulence and burping (collectively, gas) were reduced when using a composition of the present invention. Bowel urgency, which is an indication of diarrhea, was also reduced when using compositions of the invention.

The inventors also have preliminary results indicating that compositions of the invention have particular efficacy in treating indigestion and gastric reflux.

The symptoms treated by compositions of the invention are also symptoms of inflammatory bowel disorders, heartburn and IBS. As such, the results presented by the inventors provide strong evidence that compositions of the invention promote laxation thus treating constipation as well as relieving the symptoms of IBS and other gastro-intestinal disorders referred to herein.

In providing a composition for altering, maintaining and/or restoring a balance of intestinal microflora (for example bacteria) of a subject, the invention may maintain or stimulate the growth of at least one beneficial bacteria in the gut and/or inhibit or suppress the growth of at least one harmful or pathogenic bacteria in the gut. Preferably the beneficial bacteria are selected from the group comprising probiotic bacteria. More preferably the beneficial bacteria are selected from the group comprising bifidobacteria and lactobacilli. Some examples include *Lactobacillus reuteri, Lactobacillus acidophilUs, Pediococcus acidilactici*, and *Lactobacillus plantarum*. Preferably the harmful bacteria are selected from the group comprising pathogenic bacteria. More preferably the harmful bacteria are selected from the group comprising *bacteroides, Clostridia*, coliforms, and sulphate reducing bacteria. Some examples include *Escherichia coli* (for example *E. coli* 0157:H7), *Salmonella typhimurium*, and *Staphylococcus aureus*. Most preferably the harmful bacteria are selected from the group comprising gram negative pathogenic bacteria. Materials and methods for analysing levels and identity of beneficial and pathogenic gut bacteria are found in NZ554991 which is incorporated herein by reference.

The gastrointestinal health of the subject may be assessed by the incidence of symptoms associated with one or more gastrointestinal disorders which include, but are not limited to constipation, inflammatory bowel conditions, indigestion, gastric reflux, bloating, gas, abdominal pain, diarrhoea, heartburn and irritable bowel syndrome.

The dosage provided and the length of the administration programme may differ depending, for example, on the requirement for treatment, the severity of the gastrointestinal disorder, the age and/or the general health of the subject. However, by way of example, a dosage range of 375 mg to 11 g, for example 500 mg to 3 g of kiwifruit extract may be administered per day. For minor digestive dysfunction and/or gastrointestinal disorders, for altering, maintaining and/or restoring a balance of intestinal microflora of a subject and for maintaining and/or improving the gastrointestinal health of a subject, the dosage may comprise, for example a dose of approximately 1000-1300 mg per day, for example 1150 mg. For more serious digestive dysfunction and/or gastrointestinal disorders, approximately 2.5 g of kiwifruit extract may be administered per day, for example. It should be appreciated that the daily desired dose may be delivered in a single dose or two or more divided doses. In one embodiment, the composition is administered at a daily dose of 1150 mg as two unit doses of 575 mg each. Preferably, the composition is administered prior to food.

The invention will now be described, by way of example only, which reference to the following Examples and Experiments.

EXAMPLES

The kiwifruit extract referred to in the below examples is Zyactinase®, and is prepared according to the method(s) set out in WO2008/136689 or WO2006/118476. The white bean extract is StarchLite® as referred to hereinbefore.

Example 1

A large number of commercially available dietary supplements and in-house preparations were tested in combination with kiwifruit extract for synergistic activity. A number of these extracts contained protease enzymes which the inventors hypothesised would enhance the activity of the Zyactinase® enzymes. This turned out not always to be the case and instead adding further proteases appeared to block the Zyactinase® activity. From these experiments, the inventors surprisingly found that the amylase inhibitor (which is postulated to protect the proteases rather than supplement them) white bean extract stood out as being effective in enhancing the enzyme activity of the kiwifruit extract. Further tests were conducted on this extract and are detailed below.

Method

The enzyme activity of the kiwifruit extract was analysed according to the method detailed below.

The following reagents were prepared:

8% Trichloroacetic acid, 2M NaOH and 50 mM Citrate Buffer containing 10 mM EDTA. The citrate buffer was prepared using 1.05 g citric acid+80 ml deionised water+add 1 ml of 1M EDTA stock solution; take to pH 6.25 by addition of 2N NaOH and top up to 100 ml by deionised water.

Azocasein substrate solution (5 mg/ml) was prepared using both water and 50 mM citrate buffer containing 10 mM EDTA (10 ml each for every 100 mg substrate). Kiwifruit extract sample solution (50 mg/ml) was prepared using 0.2 g kiwifruit extract dissolved in 2 ml citrate buffer (50 mM citrate buffer containing 10 mM EDTA) and 2 ml distilled water The following method was used to analyse actinidin enzyme activity: 1) Add 0.25 ml of kiwifruit extract sample solution in 4 centrifuge tubes (1.5 ml capacity), two active and two blank. 2) Add 0.5 ml of 8% Trichloroacetic acid in 2 blank tubes to calibrate a zero reading. 3) Add 0.5 ml of Substrate solution in all 4 tubes. 4) Incubate all the tubes at 35° for 120 min. 5) Add 0.5 ml of 8% Trichloroacetic acid to the two active tubes. 6) Centrifuge for 5 minutes. 7) Remove two lots of 0.75 ml of supernatant into centrifuge tube; add 0.1 ml of 2N NaOH. 8) Measure absorbance at 420 nm by UV-Vis spectrophotometer in a quartz cell (optical path length: 10 mm). The initial absorbance is zeroed by blank and then the active sample is added and absorbance noted. 9) Enzyme activity in units per milligram is calculated as follows $$\frac{\text{Absorbance @ 420 nm}}{\text{Calibration factor} \times \text{Conc. of kiwifruit extract in solution (g)}} = U/g$$

White bean extract was added to kiwifruit extract in 2%, 5%, 10%, 20% and 50% concentrations (w/w). The kiwifruit extract was present at the reciprocal percentage amount. A control sample was prepared with 0% white bean extract inhibitor. The white bean extract used was Starchlite® produced by PharmaChem Laboratories Inc., New Jersey. No saliva was added to the solutions.

Results

| Concentration of white bean extract (% w/w) | Absorbance | Actinidin enzyme activity (U/g) |
|---|---|---|
| 0 | 0.620 | 198.4 |
| 2 | 0.785 | 251.2 |
| 5 | 0.515 | 164.8 |
| 10 | 0.221 | 70.72 |
| 20 | 0.495 | 158.4 |
| 50 | 0.402 | 128.64 |

Conclusions

This experiment demonstrates that 2% white bean extract added to kiwifruit extract enhances enzyme activity when compared to a control extract without white bean extract.

At higher concentrations, the amount of kiwifruit extract was reduced and therefore we would also expect a concomitant reduction in enzyme activity. Despite this expectation, it was observed that enzyme activity at 50% kiwifruit extract, 50% white bean extract was greater than the activity expected with only 50% of the enzyme present. This shows that the white bean extract is enhancing enzyme activity even at this concentration.

Example 2

The inventors used an enzyme assay (referred to as the Vital Foods method) described below to determine the enzyme activity of the kiwifruit extract. The principle of the assay relies on the ability of the enzymes to liberate milk casein as a substrate. The undigested casein is removed by precipitation using trichloroacetic acid solution, then the amount of the resultant soluble decomposition product is measured by spectrophotometric analysis absorbance in 275 nm.

Method

The following reagents are required: 0.1M hydrochloric acid test solution, 1M sodium hydroxide reagent, 0.1M sodium hydroxide reagent, 1 mg/ml tyrosine standard solution, 50 μg/ml tyrosine standard solution, 0.11M trichloroacetic acid solution, 0.05M cysteine-EDTA solution, 0.05M disodium hydrogen phosphate solution.

The cysteine-EDTA solution should be prepared according to the following method: take 70 ml of water and add 0.875 g of special grade L-cysteine monohydrochloride monohydrate; add 0.223 g of disodium ethylenediamine tetraacetic acid; control the pH into 4.50 with 1M sodium hydroxide test solution; add water to make 100 ml.

The substrate should be prepared according to the following method: weigh 1 g of milk casein (Hammerstein No. 2242 produced by Merck & Co., Inc.); dry it at 105 degrees C. for 2 hours; weigh the amount corresponding to 3.0 g of the dried matter; add 400 ml of 0.05M disodium hydrogen phosphate solution little by little so as not to generate granular lumps and apply heat to 60-70 degrees C. for 15 minutes to dissolve it therein; after cooling it, control the pH to 8.00 with 1M (or 0.1M) sodium hydroxide test solution; add water to make 500 ml.

A sample solution should be prepared according to the following method: weigh 4.0 g of sample; add distilled water to make 100 ml; dissolve the sample completely by using a vortex mixer or magnetic stirrer; leave it at 4 degrees C. for 1 hour; take 1 ml of solution and add 4 ml of 0.05M cysteine-EDTA (ethylenediamine tetraacetic) to, make the final volume to 5 ml.

The analysis procedure should be carried out according to the following method:

1. Active sample: place 5 ml of substrate in each screw cap test tube; leave them in an incubator, which has been set to 37±0.5 degrees C. in advance, for 10 minutes; add each 1 ml of sample solution and agitate it with a vortex mixer; leave them at 37±0.5 degrees C. for 10 minutes; add each 5 ml of 0.11M trichloroacetic acid solution and agitate it with the vortex mixer; leave them at 37±0.5 degrees C. for 30 minutes; centrifuge at 5000 rpm for 15 minutes; measure the absorbance ($A_t$) on this liquid in a wavelength of 275 nm using water as a control (blank).

2. Control sample: place 5 ml of 0.11M trichloroacetic acid solution in each screw cap test tube; leave them in an incubator, which has been set to 37±0.5 degrees C. in advance, for 10 minutes; add each 1 ml of sample solution and agitate it with a vortex mixer; leave them at 37±0.5 degrees C. for 10 minutes; add each 5 ml of substrate and agitate it with the vortex mixer; leave them at 37±0.5 degrees C. for 30 minutes; centrifuge at 5000 rpm for 15 minutes; measure the absorbance ($A_b$) on this liquid in a wavelength of 275 nm using water as a control (blank).

Measure absorbance $A_s$ of tyrosine standard solution at 275 nm using water as the reference. Measure absorbance $A_{so}$ of 0.1 hydrochloric acid at 275 nm using water as the reference. One unit of the enzyme activity is defined as the amount of enzyme that increases the absorbance equivalent to 1 μg of tyrosine per minute when the test is performed under the conditions of this procedure.

Enzyme activity in this product (units per gram) =

$$\frac{(A_t - A_b) \times 50}{A_s - A_{so}} \times \frac{11}{10} \times \frac{1000}{W}$$

Where W indicates the weight (mg) of the sample in 1 ml of the sample solution

The mean value of two repetitions for each sample treatment was taken to provide a measurement of actinidin enzyme activity. White bean extract at different concentrations (% w/w) was combined with kiwifruit extract (at the reciprocal percentage amount w/w) to provide 4.0 g for sample preparation as outlined above. No saliva was added to the samples.

Results

| Treatment | Enzyme Units (U/g) |
|---|---|
| White bean extract (0%) + kiwifruit extract | 5790 |
| White bean extract (1%) + kiwifruit extract | 6130 |
| White bean extract (2%) + kiwifruit extract | 5674 |
| White bean extract (5%) + kiwifruit extract | 5461 |

Conclusions

This experiment supports the conclusions from Example 1 that white bean extract added to kiwifruit extract enhances enzyme activity when compared to a control extract without white bean extract. This assay suggests that the highest enzyme activity for this particular formulation is obtained when using a white bean extract concentration of 1%.

Example 3

Method

The "Vital Foods" method outlined above was used to determine the enzyme activity of kiwifruit extract in a composition comprising white bean extract and kiwifruit extract in the presence of saliva.

4 ml of saliva was mixed with a 4 g sample of a composition comprising kiwifruit extract and white bean extract for 2 minutes. The white bean extract was present in the composition at 2% (w/w) and the kiwifruit extract was present at 98% (w/w). The mean value of two repetitions for each sample treatment was taken to provide a measurement of enzyme activity.

Results

| Treatment | Enzyme activity U/g |
| --- | --- |
| Kiwifruit extract + saliva | 4541 |
| White bean extract (2%) + kiwifruit extract + saliva | 5151 |

Conclusion

This result demonstrates that in the presence of saliva, the enzyme activity is higher if white bean extract is present. This finding supports the inventor's hypothesis that salivary amylases in the saliva are inhibiting enzyme activity of the extract.

Clinical Studies

Confidential clinical studies have been conducted in humans to determine the efficacy of a composition of the invention when formulated as a powder mixed in liquid. Results from these studies are presented in examples 4 to 7 below.

Example 4

Method

An initial trial involved three volunteer elderly subjects (female between 75 to 80 years old) with chronic constipation. These subjects normally took a regular daily dose of 10 ml of lactulose once a day (unless more was required to induce a bowel movement) for relieving chronic constipation. Lactulose dosing was stopped during the trial. These three subjects had previously used KiwiCrush (frozen Kiwifruit extract composition without WBE) and had found that 250 ml twice a day resolved their constipation.

A dose titration was set up. Four formulations were made of Kiwifruit extract plus white bean extract (Starchlite®) to test how the drink powder formulation of kiwifruit extract was working in comparison to KiwiCrush® (frozen format) and to determine whether white bean extract made any difference.

A: Kiwifruit extract (powder in liquid form)+0% White bean extract

B: Kiwifruit extract (powder in liquid form)+1% White bean extract

C: Kiwifruit extract (powder in liquid form)+2% White bean extract

D: Kiwifruit extract (powder in liquid form)+3% White bean extract

The formulations were dispensed in sachets of 10 g (with 55% Kiwifruit extract (Zyactinase®)) and administered in 250 ml of water. Two sachets were administered approximately 12 hours apart until a bowel movement occurred. 250 ml KiwiCrush® contained the same amount of kiwifruit extract (Zyactinase®) as one sachet.

Results

KixiCrush: Normal bowel movement within 24 hours of 500 ml

A: Bowel movement within 48 hours, stool was hard and 4 sachets needed to achieve bowel movement B: Semi hard bowel movement within 24 hours, 2-3 sachets required to achieve bowel movement C: Normal bowel movement within 12 hours following 2 sachets D: Bowel movement within 48 hours, stool was hard 4 sachets required to achieve bowel movement.

Conclusion

The results indicate that all formulations were effective and that in particular formulation C containing kiwifruit extract and WBE was the most effective and better than the Kiwi-Crush® formulation which did not contain the WBE.

Example 5

Method

Blind trials were undertaken at three different locations on a total of 37 subjects. Elderly subjects were chosen based on a history of chronic constipation requiring ongoing use of lactulose (a strong laxative) either due to prolonged use of various medications or simply due to old age. All subjects were aged between 65 to 95 years old. Subjects were provided the treatment and the number of bowel movements within the next 24 hours was recorded by nursing staff, as well as whether lactulose was required and the required dose.

Four formulations containing varying concentrations of white bean extract

A: Kiwifruit extract (powder in liquid form)+0% White bean extract

B: Kiwifruit extract (powder in liquid form)+1% White bean extract

C: Kiwifruit extract (powder in liquid form)+2% White bean extract

D: Kiwifruit extract (powder in liquid form)+3% White bean extract

Kiwifruit extract was present in the dose at a concentration of 55% for each formulation. The compositions were administered as a powder for suspension in water. One sachet of powder contained 10 g of formulation. The white bean extract used was StarchLite® and the kiwifruit extract used was Zyactinase®.

All of these facilities were currently using KiwiCrush® at the time and thus this was a comparison between the powder and frozen format A preliminary trial was conducted on 17 of the subjects with the following results:

KiwiCrush®: Subjects were having generally normal bowel movements within 24 hours on one to two glasses (250 ml) per day A: Bowel movement within 24 hours, stool was harder than usual and needed to take up to 2 sachets B: Semi hard bowel movement within 24 hours, needed 1-2 sachets C: Normal bowel movement with 12 hours on 1-2 sachets No bloating or abdominal discomfort was reported.

Following this preliminary trial, a more robust trial was conducted with 20 subjects over nine days. One sachet (10 g) of composition was administered as a powder suspension in water formulation prior to the evening meal on day one. Treatment on day one was followed by one week of normal (i.e. lactulose only) treatment followed by a second day of treatments on day 9. Treatments were randomly assigned and swapped during the day 9 treatment.

Results

Day 1 results summary:

Treatment A (0%)=limited help with bowel movement, high dose of lactulose required Treatment B (1%)=bowels working sufficiently without the need for lactulose Treatment C (2%)=good bowel movements, no lactulose required Treatment D (3%)=some help but complemented by a dose of lactulose Using one sachet of the 2% composition, at least one bowel movement was obtained in less than 12 hours. Using the same amount of the 3% composition, bowel movements did not occur and lactulose at the normal dosage was required for bowel movement to occur. 0% treatment resulted in little help with bowel movement and a high dose of lactulose was required. The 1% composition was effective but lactulose was still required to induce bowel movements.

Day 9 results supported the results from day 1 which showed that the 2% composition resulted in most bowel movements and least lactulose required.

Conclusion

These results show that a composition comprising white bean extract and a kiwifruit extract has increased efficacy for increasing bowel movements and therefore reducing the incidence of constipation when compared to a kiwifruit extract alone. Additionally, the results show that the 2% white bean extract composition was the most effective for increasing bowel movements. The reduction in constipation may also lead to a reduction in associated gastrointestinal disorders.

Example 6

Method

A further trial was conducted for one week with 2 doses of a 10 g formulation containing 2% white bean extract, 98% Kiwifruit extract in 250 ml of water, administered twice a day.

Results

The amount of lactulose required declined over the period to 2 ml or no lactulose. All subjects receiving the composition comprising 2% white bean extract reported less urgency, reduced flatulence, wind and bloating.

Conclusion

These results show that a composition comprising white bean extract and a kiwifruit extract has increased efficacy for increasing bowel movements and therefore reducing the incidence of constipation when compared to a kiwifruit extract alone.

Example 7

Method

The investigational product for this double blinded placebo controlled clinical trial was Kivia Powder (Vital Food Processors Ltd, Auckland, New Zealand), containing the active ingredient Zyactinase® at a dose of 5.5 g per 10 g dose (55%). Kivia Powder is an extract of kiwifruit. Additional ingredients included apple powder, fructose, lemon powder, vital spirulina, citric acid, tropical flavor, sucralose, and white kidney bean extract (2% w/w). The placebo was a combination of inactive components, including lemon powder, vital spirulina, citric acid, fructose, sucralose, and tropical flavor.

87 subjects were included in the study, all being healthy men (n=32) and women (n=55), between 18 and 65 years of age with a body mass index (BMI) between 20-35 kg/m2. Mean age for each group was 38±14 years for the Treatment group and 41±14 years for the Placebo group. The subjects had symptoms consistent with Occasional Constipation defined as three or fewer defecations per week plus at least 1 of the following during the 0.2 week run-in period:

Straining during at least 25 percent of defecations.

Lumpy or hard stools in at least 25 percent of defecations.

Sensation of incomplete evacuation for at least 25 percent of defecations.

Sensation of anorectal obstruction/blockage for at least 25 percent of defecations.

Manual manoeuvres to facilitate at least 25 percent of defecations (eg, digital evacuation, support of the pelvic floor).

The study was a randomized, double-blind, placebo-controlled parallel-design study where subjects took either a) the study product or b) a placebo, daily for four weeks.

The study was conducted at the Staywell Research clinical research site located in Northridge, Calif. and Medicus Research was the CRO for this study. IRB approval was received (Copernicus Group IRB, Cary, N.C.) prior to the initiation of any study related activities. The numbers of spontaneous bowel movements and complete spontaneous bowel movements were investigated. The secondary objective was to determine the efficacy of a composition of the invention compared to placebo on gut health based on diary information. Endpoints included stool form (Bristol Stool Scale), bowel urgency, abdominal bloating, abdominal discomfort, satisfaction with bowl habits, flatulence and burping.

Results

Figure 2:
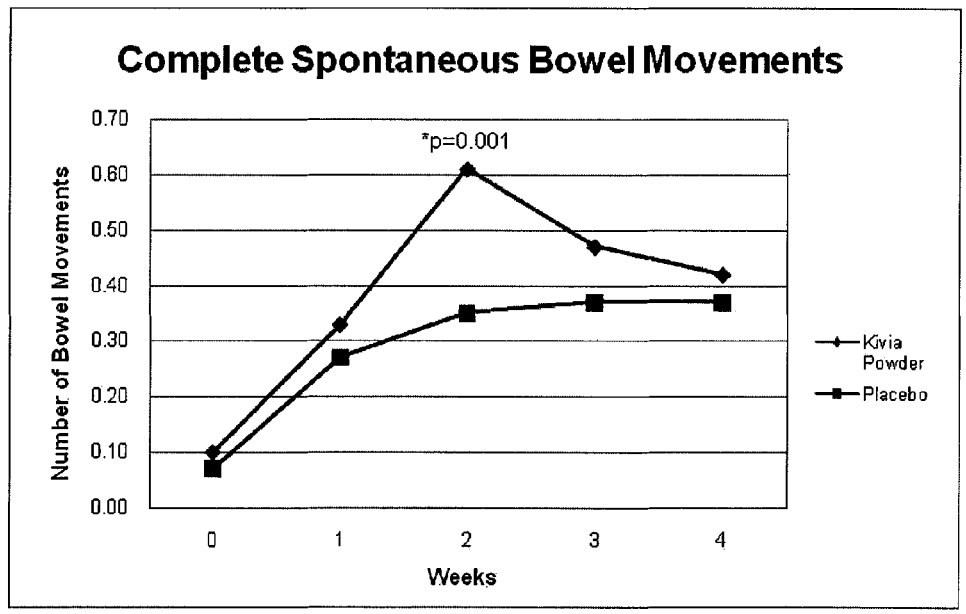
FIG. 2 shows the number of complete spontaneous bowel movements over a four week trial of a composition of the invention.

The primary endpoint of this study was bowel movement frequency. The numbers of spontaneous bowel movements (SBM)(FIG. 1) and complete spontaneous bowel movements (CSBM)(FIG. 2) were investigated. A complete spontaneous bowel movement is a bowel movement during which the subject answered "yes" to the question "Have you completely emptied your bowel?".

By week 3, the average number of SBM was significantly higher in the group obtaining a composition of the invention (p=0.000) and this difference remained statistically significant at week 4 (p=0.020).

By week 2, the average number of CSBM was significantly higher in the group obtaining a composition of the invention (p=0.001).

Figure 3:
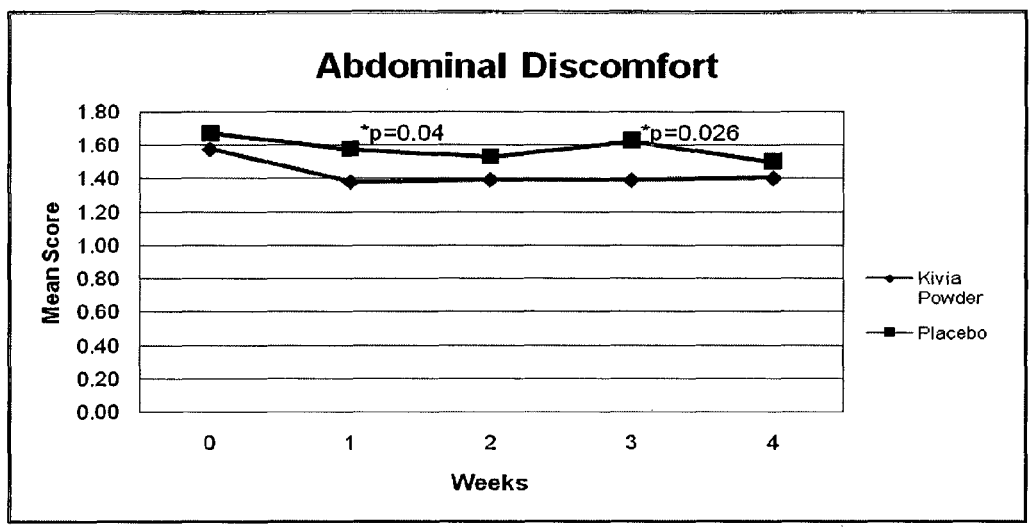
FIG. 3 shows the degree of abdominal discomfort over a four week trial of a composition of the invention
Figure 4:
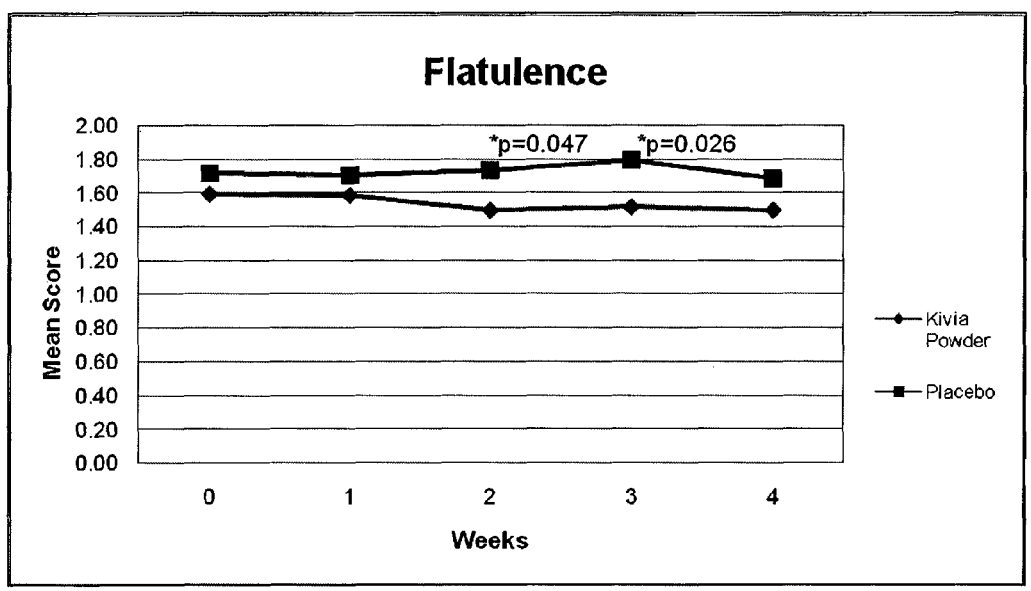
FIG. 4 shows the degree of flatulence over a four week trial of a composition of the invention

Abdominal discomfort or pain (FIG. 3) was significantly lower in the group obtaining a composition of the invention at weeks 1 and 3 (p<0.05) and flatulence (FIG. 4) was significantly lower in the group obtaining a composition of the invention at weeks 2 and 3 (p<0.05).

Figure 5:
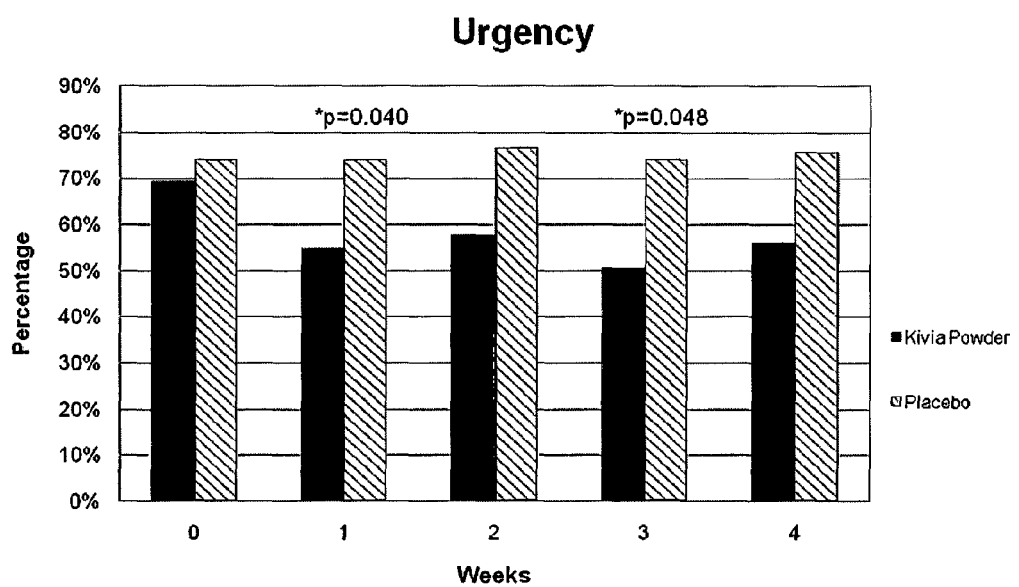
FIG. 5 shows the bowel urgency over a four week trial of a composition of the invention

Bowel urgency (FIG. 5) was reduced in the treatment group vs. the placebo group from weeks 2 to 5. The percent reduction (active vs. placebo) in bowel urgency at weeks 2 to 5 were respectively, −26% (p<0.05), −25%, −32% (p<0.05), and −26%.

Between group comparisons demonstrated that by week 2, there were significantly more Type 4 Bowel movements (sausage shaped and smooth) in the group obtaining a composition of the invention compared to the placebo group (p=0.020) and by week 3 there were significantly more Type 5 Bowel movements (soft blobs with clear cut edges) in the group obtaining a composition of the invention compared to the placebo group (p=0.041).

Conclusion

In a population with occasional constipation, compositions of the invention appear to significantly increase the frequency of Spontaneous Bowel Movements and Complete Spontaneous Bowel Movements, as well as reduce the severity of abdominal discomfort, frequency of flatulence, and urgency associated with bowel movements when compared to placebo. The composition also improved stool form compared to placebo and did not cause any increase in burping. The product was safely administered for 4 weeks.

Example 8

A higher stability and extended shelf life is a desirable characteristic for consumers and vendors of the composition. The inventors found that the compositions of the invention have an unexpectedly high stability and shelf life.

Method

Each product was stored at room temperature (20° C.-35° C.) and 60% RH in plastic bottles. Actinidin enzyme activity was analysed according to the method outlined in Example 1. Analyses were carried out at set time points (including a control at time=0).

The compositions contained the following ingredients:

Tablets—Di-Pac® tableting sugar (Domino Specialty Ingredients, Florida USA), tropical flavour, natural intense sweetener, magnesium stearate, silicon dioxide, StarchLite (1.98%) and Zyactinase® (69.15%).

Soft chew—evaporated cane juice, rice syrup, fructose, sunflower lecithin, natural flavors, corn starch, glycerin, sunflower oil, natural color from chlorophyll, StarchLite (1.6%) and Zyactinase® (15.38%).

Powder for suspension in a liquid—apple powder, citric Acid, lyophilized lemon, fructose, sucralose, copper chlorophyll, tropical flavour, Starchlite (2%), Zyactinase® (55%), Results Powder for Suspension in a Liquid

| Time Interval | Actinidin enzyme Activity (U/g) |
|---|---|
| 0 time | 4600 |
| 2 weeks | 4602 |
| 4 weeks | 4556 |

Tablets

| Time Interval | Actinidin enzyme Activity (U/g) |
|---|---|
| 0 time | 2001 |
| 1 month | 1967 |

Chews

| Time Interval | Actinidin enzyme Activity (U/g) |
|---|---|
| 0 time | 1041 |
| 1 month | 805 |
| 2 months | 795 |
| 3 months | 790 |

Conclusion

The substantial maintenance of the enzyme activity over a period of months indicates suitability of products of the invention for product use.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

Furthermore, titles, headings, or the like are provided to enhance the reader's comprehension of this document, and should not be read as limiting the scope of the present invention.

The reference to any prior art in this specification is not, and should not be taken as, an acknowledgment or any form of suggestion that that prior art forms part of the common general knowledge in any country in the world.

The entire disclosures of all applications, patents and publications, cited above and below, if any, are hereby incorporated by reference.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

REFERENCES

Boron, W. F. (2003). Medical Physiology: A Cellular And Molecular Approaoch. Elsevier/Saunders. pp. 1300

Mosolov, V. V. Grigor'eva, L. I., Valureva, T. A. (2001) Plant proteinase inhibitors as multifunctional proteins (Review). Applied Biochemistry and Microbiology 37(6) 545-551.

Obiro, W. C., Zhang, T., Jiang, B., (2008). The nutraceutical role of the *Phaseolus vulgaris* α-amylase inhibitor. British Journal of Nutrition, 100: 1-12

Rakhimova, S. K., Mejlumyan, L. G., Yuldashev, P. H., and Sagdullaev, B. T. (2008). Bifunctional inhibitor from corn cultivated in Uzbekistan. Chemistry of Natural Compounds Vol 44, (1), 59-62.

Sharma A, Gupta M. N. (2001). Three phase partitioning as a large-scale separation method for purification of a wheat germ bifunctional protease/amylase inhibitor. Process Biochemistry 37(2) 193-196.

Schroder R, Nicholas P, Vincent S. J, Fischer M, Reymond S, and Redgewell R. J. (2001) Purification and characterisation of a galactomannan from kiwifruit (*Actinidia delicisiosa*). Carbohyr Res. April 12: 331 (3) 291-306.

Reid, J. D., Hussain, S., Bailey, T. S. F., Sonkaria, S., Sreedharan, S. K., Thomas E. W., Resmini, M., Brocklehurst, K. (2004). Isomerization of the uncomplexed actinidin molecule: kinetic accessibility of additional steps in enzyme catalysis provided by solvent perturbation. Biochem. J. 378, 699-703

The invention claimed is:
1. A composition comprising:
a kiwifruit extract derived from processed kiwifruit pulp without seeds, wherein the kiwifruit extract comprises at least one cysteine protease enzyme;
an extract comprising an amylase inhibitor and/or a bifunctional protease-amylase inhibitor which binds loosely to the at least one cysteine protease enzyme of the kiwifruit extract, and wherein said extract is not derived from kiwifruit; and
one or more suitable diluents, carriers and/or excipients.
2. The composition of claim 1, wherein the kiwifruit extract has an actinidin enzyme activity in the range of 1500 U/g to 6000 U/g.
3. The composition of claim 1, wherein the extract comprising an amylase inhibitor and/or bifunctional protease-amylase inhibitor is an extract from a plant in the legume family, or is an extract from a plant or seed selected from the group consisting of white kidney bean, wheat, *Lens culinaris*, *Psophocarpus tetragonolobus*, *Cicer arietinum*, *Vigna aconitifolia*, oats, sorghum, rye, barley, mango seeds, and potatoes.
4. The composition of claim 1, wherein the extract comprising an amylase inhibitor and/or bifunctional protease-amylase inhibitor comprises white kidney bean extract.
5. The composition of claim 1, wherein the bifunctional protease-amylase inhibitor is at least one selected from the group consisting of a serine protease-amylase inhibitor, a trypsin-amylase inhibitor, and a suppressor of the activity of trypsin and α-amylase.
6. The composition of claim 1, wherein the extract comprising an amylase inhibitor and/or bifunctional protease-amylase inhibitor is present in the composition at a minimum concentration of approximately 0.5% (w/w) and at a maximum concentration of approximately 50% (w/w).
7. The composition of claim 1, wherein the ratio of kiwifruit extract:extract comprising an amylase inhibitor and/or bifunctional protease-amylase inhibitor is between approximately 200:1 and 1:1 (w/w).
8. The composition of claim 1, wherein the kiwifruit extract concentration and the extract comprising an amylase inhibitor concentration is at least one selected from the group consisting of:
kiwifruit extract at a concentration of approximately 98 to 99.5% (w/w) and extract comprising an amylase inhibitor at approximately 0.5 to 2.0% (w/w),
kiwifruit extract at a concentration of approximately 97.5 to 99.5% (w/w) and extract comprising a bifunctional protease-amylase inhibitor at a concentration of approximately 0.5 to 2.5% (w/w),
extract comprising an amylase inhibitor at approximately 1.98% (w/w) and a kiwifruit extract at approximately 69.15% (w/w),
extract comprising an amylase inhibitor at approximately 2% (w/w) and a kiwifruit extract at approximately 55% (w/w),
extract comprising an amylase inhibitor at approximately 1.6% (w/w) and a kiwifruit extract at approximately 15.38% (w/w),
extract comprising a bifunctional protease-amylase inhibitor at a concentration of approximately 1.98% (w/w) and a kiwifruit extract at approximately 69.15% (w/w),
extract comprising a bifunctional protease-amylase inhibitor at a concentration of approximately 2% (w/w) and a kiwifruit extract at approximately 55% (w/w), and
extract comprising a bifunctional protease-amylase inhibitor at a concentration of approximately 1.6% (w/w) and kiwifruit extract at approximately 15.38% (w/w).
9. The composition of claim 1, wherein the composition is formulated in a form selected from the group consisting of tablet form, chewable tablet form, soft chew form, powder form, powder form for suspension in a liquid, capsule form, liquid form and soft gel form.
10. The composition of claim 1, wherein the at least one cysteine protease enzyme comprises actinidin.
11. The composition of claim 10, wherein the kiwifruit extract further comprises fiber and prebiotic material.
12. The composition of claim 1, wherein the ratio of kiwifruit extract:extract comprising amylase inhibitor and/or bifunctional protease-amylase inhibitor is approximately 34.9:1 (w/w).
13. The composition of claim 1, wherein the ratio of kiwifruit extract:extract comprising amylase inhibitor and/or bifunctional protease-amylase inhibitor is approximately 27.5:1 (w/w).
14. The composition of claim 1, wherein the ratio of kiwifruit extract:extract comprising amylase inhibitor and/or bifunctional protease-amylase inhibitor is approximately 9.6:1 (w/w).
15. A method for treating at least one of digestive dysfunction, a gastrointestinal disorder, and symptoms associated with a digestive disorder or a gastrointestinal disorder, of a subject in need thereof, comprising administering to the subject an effective amount of the composition of claim 1.
16. A method for altering, maintaining, or restoring a balance of intestinal microflora, of a subject in need thereof, comprising administering to the subject an effective amount of the composition of claim 1.
17. The method of claim 16, wherein the administration of the composition promotes the amount, growth or efficacy of beneficial gut bacteria in the subject.
18. The method of claim 16, wherein the administration of the composition reduces the amount, growth or efficacy of pathogenic gut bacteria in the subject.
19. A method for promoting one or more of the following in a subject in need thereof:
an increase in spontaneous bowel movements,
an increase in complete spontaneous bowel movements,
a decrease in abdominal discomfort or pain,
a decrease in flatulence,
a decrease in bowel urgency,
a decrease in wind or burping, and
a decrease in bloating,
comprising administering to the subject an effective amount of the composition of claim 1.

* * * * *